United States Patent
Kranz

[11] Patent Number: 5,156,628
[45] Date of Patent: Oct. 20, 1992

[54] SHAFT PROSTHESIS

[75] Inventor: Curt Kranz, Berlin, Fed. Rep. of Germany

[73] Assignee: Johnson & Johnson Professional Products GmbH, Norderstedt, Fed. Rep. of Germany

[21] Appl. No.: 802,276

[22] Filed: Dec. 4, 1991

[30] Foreign Application Priority Data

Dec. 12, 1990 [DE] Fed. Rep. of Germany ....... 4040106

[51] Int. Cl.$^5$ ............................ A61F 2/36; A61F 2/30
[52] U.S. Cl. ......................................... 623/23; 623/16
[58] Field of Search ...................... 623/23, 22, 18, 16

[56] References Cited

U.S. PATENT DOCUMENTS

| | | | |
|---|---|---|---|
| 4,101,985 | 7/1978 | Baumann et al. | 623/22 |
| 4,664,668 | 12/1987 | Beck et al. | 623/23 |
| 4,718,914 | 1/1988 | Frey et al. | 623/23 |

FOREIGN PATENT DOCUMENTS

| | | | |
|---|---|---|---|
| 2933237 | 3/1981 | Fed. Rep. of Germany | 623/22 |
| 3844157 | 6/1990 | Fed. Rep. of Germany | 623/23 |

*Primary Examiner*—Ronald Frinks
*Attorney, Agent, or Firm*—Spencer, Frank & Schneider

[57] ABSTRACT

A prosthesis includes a tubular, curved shaft having a shaft cavity, a length, proximal and distal ends; and an outer diameter and a wall thickness both decreasing towards the distal end. The shaft cavity is closed throughout, and the tubular shaft has, in a zone of the distal end, a flattened, essentially plate-shaped wall portion having a length coextensive with the length of the shaft, and a thickness of approximately between 0.5 and 1.5 mm.

13 Claims, 2 Drawing Sheets

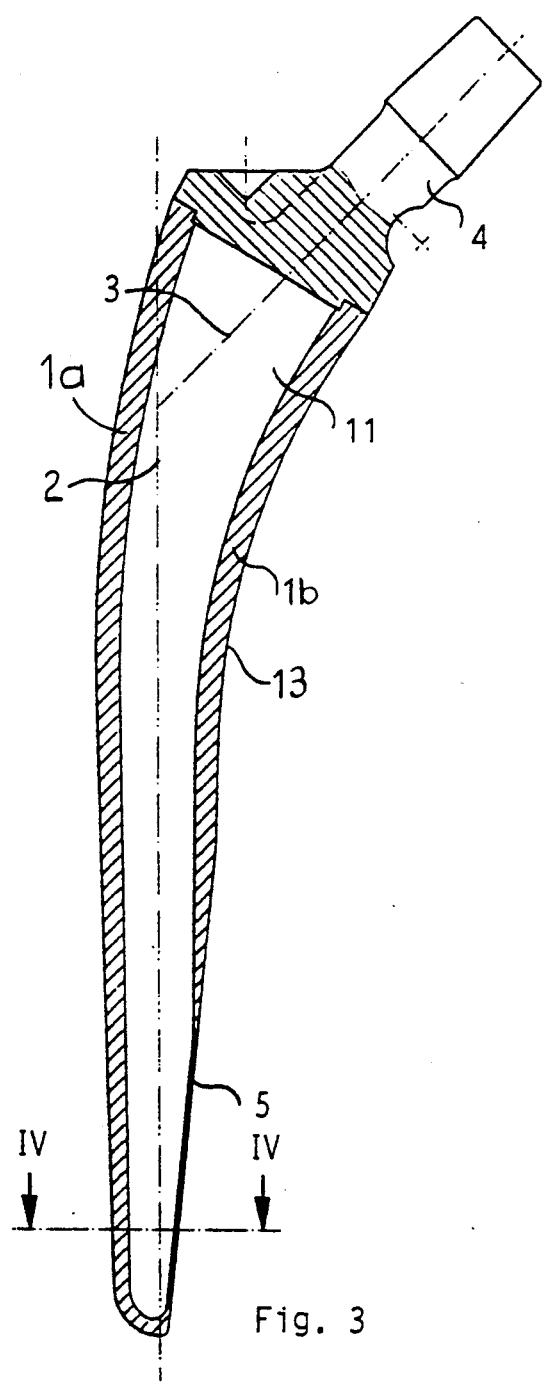
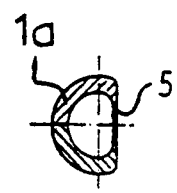
Fig. 3
Fig. 4

SHAFT PROSTHESIS

BACKGROUND OF THE INVENTION

The invention relates to a shaft prosthesis, particularly a hip joint prosthesis having a tubular, curved hollow shaft which is tapered diametrically and in thickness and whose flexural rigidity decreases from its proximal end to its distal end at a relatively greater rate than its longitudinal rigidity. For a cement-free implantation, such an endoprosthesis is hammered into the correspondingly prepared (for example, pre-filed) bone cavity for a press-fit connection with the bone.

German Offenlegungsschrift 29 33 237 discloses a prosthesis shaft whose local elasticity and rigidity is adapted to the surrounding bone regions. This adaptation, however, relates only to cross-sectional dimensions and their coordination with forces acting in the direction of the longitudinal axis. Cross section and wall thickness decrease continuously from the upper to the lower end of the prosthesis shaft. It is a disadvantage of this construction that the deformations occurring as a result of forces attacking outside of the longitudinal axis do not conform in their behavior to the corresponding deformations of the adjacent bone region. Thus micromovements and local loosening of the prosthesis may occur.

German Offenlegungsschrift 38 44 157 discloses an endoprosthesis which is provided with a curved shaft that can be implanted into the bone cavity and is tapered in diameter and material thickness in such a way that the flexural rigidity of the shaft decreases to a relatively greater degree than its longitudinal rigidity from its end near the joint (proximal end) to its end remote from the joint (distal end). This is accomplished in this construction by reducing the flexural rigidity by providing a cut-out region extending to the end remote from the joint and disposed along the interior of the curvature of the prosthesis shaft.

It is a disadvantage of the above-noted solution that the interior of the shaft is accessible from the bottom and is thus exposed to undesirable effects during its implanted life.

SUMMARY OF THE INVENTION

It is an object of the invention to provide an improved prosthesis of the above-discussed type, in which the positive influence of the adaptation of the deformability to the corresponding characteristics of the cortical tube of the bone, achieved by the structural configuration of the prosthesis shaft, is ensured over the period of implantation by preventing bone tissue from penetrating into the interior of the shaft.

This object and others to become apparent as the specification progresses, are accomplished by the invention, according to which, briefly stated, the prosthesis includes a tubular, curved shaft having a shaft cavity, a length, proximal and distal ends; and an outer diameter and a wall thickness both decreasing towards the distal end. The shaft cavity is closed throughout, and the tubular shaft has, in a zone of the distal end, a flattened, essentially plate-shaped wall portion having a length coextensive with the length of the shaft, and a thickness of approximately between 0.5 and 1.5 mm.

The invention is based on the recognition that the prior art endoprostheses, except for the isoelastic type, have a flexural and longitudinal rigidity which is significantly higher than that of the cortical bone tube and thus cause the cortex layer to be stress-relieved. The simultaneously resulting sudden change in rigidity at the shaft end remote from the joint leads to irregularities in the distribution of tension in an implanted prosthesis. The sudden rise in longitudinal tension results in increased callus formation due to irritation of the cortex layer. The resulting pedestal formation, however, constitutes an impediment for the actually desirable slight post-surgical settling and for the required re-anchoring of the prosthesis shaft. Moreover, the deviation from physiologically normal conditions continues to increase.

In contrast thereto, the prosthesis according to the invention prevents a sudden change in tension — while simultaneously providing sufficient flexural and longitudinal rigidity in the proximal region — due to the reduced flexural rigidity in the distal region. The result is a longitudinal rigidity which decreases — non-linearly — from the proximal end of the shaft to the distal end thereof and provides for a uniform and physiologically favorable introduction of force into the bone. The flexural rigidity initially decreases considerably from the proximal end to the distal end, to continue to drop at a much lesser rate in the distal end (approximately the remaining third of the shaft length).

In the conventional open configuration of the shaft, designed exclusively for obtaining the desired strength, some of the resulting advantages are adversely affected by the fact that bone substance is able to grow into the interior of the prosthesis. Closing off the prosthesis shaft with the conventional wall thickness would cancel out the desired strength characteristics.

It has been found that the measures according to the invention allow a sealing of the interior of the prosthesis while maintaining the desired characteristics due to the selection of an appropriately reduced wall thickness. Thus, the wall thickness in the above-noted region is selected in such a way that, on the one hand, no increase in the flexural rigidity can occur in the distal region which would adversely affect the desired strength characteristics of the prosthesis, but, on the other hand, the penetration of bone material into the interior of the prosthesis is prevented during implantation and during its implanted life. Bone substance growing into the interior of the prosthesis not only impedes a later removal of the conventional shaft (because the shaft interior open toward the distal end cannot be reached by tools for the purpose of excavation), but the strength characteristics also change. This is so, because in the region of the distal end, the bone material surrounding the free end of the prosthesis on the interior and the exterior blocks the natural movement of the prosthesis shaft, which would be desirable because of the elasticity of the prosthesis.

According to an advantageous feature of the invention, the shaft has a hollow tubular shape which tapers toward the distal end and whose wall thickness decreases uniformly, wherein the outwardly curved, lateral region of the half tube at the distal end lies opposite a medial region having a suitably reduced wall thickness. In the region of the distal shaft end which, according to the invention, is covered by a plate-shaped region having a very thin wall thickness and forms the flat side of a tube having a generally semicircular cross section, the flexural rigidity — which includes the geometrical moment of inertia — decreases considerably while the longitudinal rigidity determined by the material cross section decreases only slightly.

By virtue of the local adaptation of the flexural rigidity of the prosthesis shaft to that of the surrounding bone obtained in spite of the closed configuration according to the invention, the principle is adhered to that the longitudinal rigidity of the shaft, following the principle of an adapted deformation, has the capability (which increases considerably toward the distal end) of following the flexure of the tubular bone under load.

The selection of a closed, half-tube shape for the shaft at the distal end thereof ensures — in addition to the desired favorable course of the flexural and longitudinal rigidity curves — that no essentially irreversible growth of bone material into the shaft cavity will take place. Such an occurrence would lead to considerable difficulties during a re-implantation and the associated removal of the original prosthesis shaft.

According to a further feature of the invention, in case the local rigidity achievable by reducing the wall cross section over the length of the shaft is not sufficient, a special profile is provided in the region of Shenton's arch. Preferably, the profile should not be provided at the convex side of the shaft where it has its maximum outward curvature but on the exterior faces of the lateral half shell of the shaft parallel to the plane of the maximum curvature of the shaft in the region of Shenton's arch.

According to a further advantageous feature of the invention, the profile on the exterior face of the shaft is composed of round nubs having a spherical surface. The highest profile points lie on an imaginary line forming a continuation of an unprofiled shaft surface.

The profile depth is advantageously so selected that, on the one hand, the desired rigidity curve of the hollow shaft is obtained and, on the other hand, the possibility of formation of an irreversible bond between the shaft and the bone material is eliminated.

In accordance with another feature of the invention, a ratio of less than 1:4 has been found to be particularly advantageous between the shaft wall thickness and the profile depth on the shaft surface. The same ratio is selected between the height and maximum diameter of the individual nubs which constitute the profiled region of the shaft.

BRIEF DESCRIPTION OF THE DRAWING

FIG. 3 is a sectional elevational view of the shaft prosthesis of FIG. 1 in the lateral-medial plane.

FIG. 4 is a sectional view taken along line IV—IV of FIG. 3.

DESCRIPTION OF THE PREFERRED EMBODIMENT

Figures 1, 2:
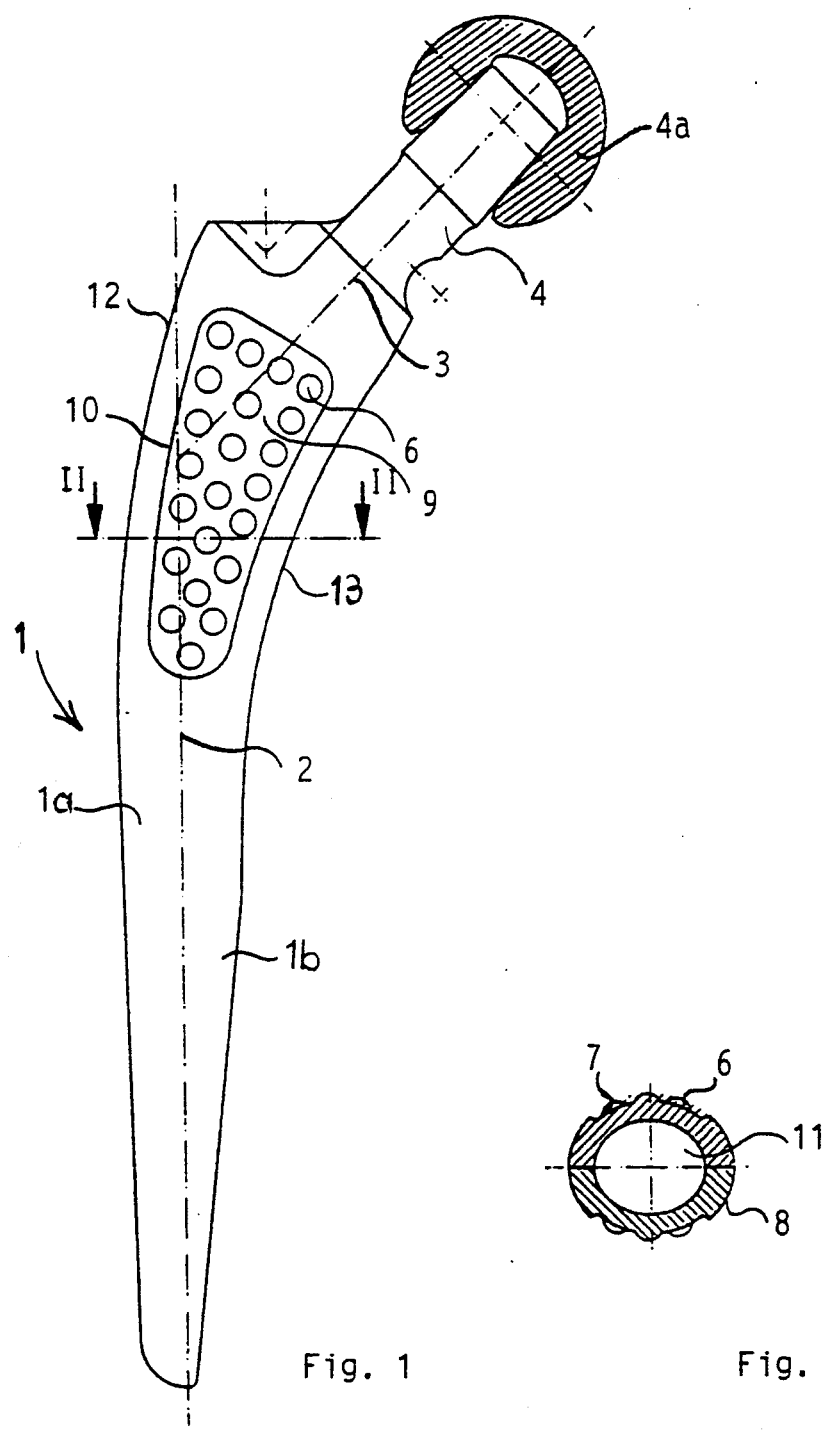
FIG. 1 is an elevational view of a shaft prosthesis according to a preferred embodiment of the invention.
FIG. 2 is a sectional view taken along line II—II of FIG. 1.

Turning to FIG 1, the shaft 1 of a hip joint shaft prosthesis according to the invention is composed of two pressed or forged half shells 1a, 1b welded together and composed of a body-compatible titanium alloy. The half shell 1b forms the interior, medial portion and the other half shell 1a forms the exterior, lateral portion of shaft 1. The parting line is curvilinear, approaching in its end regions the center lines 2 and shown in dash-dot lines. The exterior shape of shaft 1 approximately corresponds to that of a slightly bent conical tube and is thus adapted to the natural shape of the excavated marrow cavity of the femur. The cone end of prosthesis neck 4 is provided with a joint ball 4a.

A profiled surface region 9 in the zone of Shenton's arch is bounded by line 10, whose distance from the lateral envelope curve 12 and from the medial envelope curve 13, respectively, corresponds to the respective wall thickness of shaft 1.

FIG. 2 shows the inventive shape and arrangement of the nub-like profile of the prosthesis shaft in the region of Shenton's arch. The highest points 6 of nubs 7 lie — when viewed in cross section — on an imaginary line corresponding to the extended envelope curve 8 of an unprofiled shaft surface. The profiled surface 9 as projected on a cross-sectional plane essentially corresponds to the cross-sectional area of the cavity 11 enclosed by the shaft. As concerns the required mechanical characteristics of the shaft, it has been found to be advantageous to select a value of approximately one to four for the ratio of profile depth to material thickness of the shaft wall and for the ratio of the height of the nubs to the maximum nub diameter.

Turning to FIG. 3, in a zone where the thickness of the material is reduced in order to reduce flexural rigidity, a flattened, essentially plate-shaped region 5 is provided as a cover for the cavity of the shaft. The wall thickness of this region has such a small dimension (essentially 1 mm) that in spite of hermetically sealing the interior, it does not significantly increase the local flexural rigidity.

By providing the distal region of half shell 1b with the plate-shaped region 5, the shaft has, in the distal region, the general shape of a tube having a semicircular cross section, as shown in FIG. 4. The wall thickness of the plate-shaped region 5 is selected to be extremely thin compared to the remaining thickness of the shaft wall material and is constant over the entire region.

The illustration in the drawing indicates how the material thickness of the shaft walls decreases continuously from the joint toward the distal end of the shaft in half shell 1b (medial shaft portion) as well as in half shell 1a (lateral shaft portion). The plate-shaped region 5 is inclined more toward the center line of the shaft in the direction of the distal shaft end than in the oppositely disposed region of the lateral half shell 1a. These structural measures ensure the required longitudinal and flexural rigidity curves along the shaft.

The length of plate-shaped region 5 approximately corresponds to one-third of the total length of the hollow shaft up to the neck portion 4 which closes off the proximal end of the shaft.

FIG. 3 shows that the region of the small wall thickness is a continuation, toward the distal end, of the interior face 13 of the region of maximum curvature of the hollow shaft. The plate-shaped region 5 has a constant wall thickness, and the wall thickness of the shaft continuously decreases along a length portion which is situated longitudinally adjacent the plate-shaped region 5 and the size of which essentially corresponds to one-half of the length of the plate-shaped region 5.

In a section disposed ahead of the plate-shaped region 5, the shaft cross section tapers more toward the distal end than in the region subsequent thereto which includes the plate-shaped region 5.

The plate-shaped region 5 is, with respect to the center axis of the shaft, inclined more toward the shaft end than the wall region opposite thereto on the other side of the center axis of the shaft.

The closed surface of prosthesis shaft 1 obtained by the measures according to the invention prevents the irreversible growth of bone material into the cavity of the shaft and thus permits a later removal of the prosthesis if such a measure proves to be necessary.

It will be understood that the above description of the present invention is susceptible to various modifications, changes and adaptations, and the same are intended to be comprehended within the meaning and range of equivalents of the appended claims.

What is claimed is:

1. In a prosthesis including a tubular, curved shaft having a shaft cavity, a length, proximal and distal ends; said shaft having an outer diameter and a wall thickness both decreasing towards the distal end; the improvement wherein said shaft cavity is closed throughout and further wherein said tubular shaft has, in a zone of the distal end, a flattened, essentially plate-shaped wall portion having a length coextensive with the length of the shaft, and a thickness of approximately between 0.5 and 1.5 mm.

2. A prosthesis as defined in claim 1, wherein the length portion of said plate-shaped wall portion is approximately one third the length of said shaft.

3. A prosthesis as defined in claim 1, wherein said shaft has, along said plate-shaped wall portion, the shape of a tube of essentially semicircular cross section.

4. A prosthesis as defined in claim 1, wherein said shaft is formed of two longitudinal half shells secured to one another.

5. A prosthesis as defined in claim 1, wherein said shaft is curved and has an inner, medial part and an outer, lateral part; said plate-shaped wall portion being situated in said medial part.

6. A prosthesis as defined in claim 5, wherein said plate-shaped wall portion has a substantially uniform wall thickness and further wherein the medial part has a portion adjoining said plate-shaped wall portion and having a length substantially one half of the length of said plate-shaped wall portion; said portion of said medial part having a continuously decreasing wall thickness.

7. A prosthesis as defined in claim 1, wherein said shaft has a first length portion situated between said plate-shaped wall portion and said proximal end; a second length portion situated between said first length portion and said distal end and including said plate-shaped wall portion; said shaft having a cross-sectional area decreasing in said first length portion at a greater rate towards said distal end than in said second length portion.

8. A prosthesis as defined in claim 7, wherein said shaft has a longitudinal axis and further wherein said plate-shaped wall portion has a steeper inclination relative to said longitudinal axis towards said distal end than a shaft length portion situated diametrically opposite said plate-shaped wall portion.

9. A prosthesis as defined in claim 1, wherein said shaft has a profiled outer surface portion.

10. A prosthesis as defined in claim 9, wherein said profiled outer surface portion comprises a plurality of spacedly distributed nubs having a spherical surface.

11. A prosthesis as defined in claim 10, wherein said shaft has a non-profiled surface adjoining said profiled outer surface portion; said non-profiled surface having a surface contour situated at least as high as the highest elevation of said nubs; the profiled outer surface portion having a depth whose ratio to the wall thickness of the shaft is less than 1:4.

12. A prosthesis as defined in claim 9, wherein said shaft has a Shenton's arch; and further wherein said profiled outer surface portion extends in a region of Shenton's arch parallel to a plane of maximum curvature of the shaft.

13. A prosthesis as defined in claim 12, wherein a profiled outer surface portion is provided on opposite sides of said shaft.

* * * * *